United States Patent [19]

Nagae et al.

[11] Patent Number: 5,234,799
[45] Date of Patent: Aug. 10, 1993

[54] PHOTOCHROMIC MATERIAL AND REWRITABLE OPTICAL RECORDING MEDIUM

[75] Inventors: Suguru Nagae; Sei Tsuroda; Kenji Nomura; Kazuhiko Tsutsumi; Yoshiyuki Nakaki, all of Amagasaki, Japan

[73] Assignee: Mitsubishi Denki Kabushiki Kaisha, Japan

[21] Appl. No.: 856,251

[22] Filed: Mar. 25, 1992

Related U.S. Application Data

[62] Division of Ser. No. 655,999, Feb. 14, 1991, Pat. No. 5,164,287.

[30] Foreign Application Priority Data

Feb. 17, 1990 [JP] Japan ............................. 2-36643
Mar. 7, 1990 [JP] Japan ............................. 2-56858

[51] Int. Cl.⁵ .............................................. G11B 7/24
[52] U.S. Cl. ........................................ 430/345; 430/495; 430/945; 430/20; 430/19; 430/962; 359/103; 346/135.1
[58] Field of Search ........................ 430/495, 945, 20, 19, 430/270, 962, 345; 365/108; 346/135.1; 369/275.2, 288; 359/103

[56] References Cited

U.S. PATENT DOCUMENTS

| | | | |
|---|---|---|---|
| 3,642,484 | 2/1972 | Poot et al. | 430/345 |
| 4,565,779 | 1/1986 | Arakawa et al. | 430/962 |
| 4,927,917 | 5/1990 | Krongauz et al. | 534/567 |
| 5,023,859 | 6/1991 | Eich et al. | 365/113 |
| 5,024,784 | 6/1991 | Eich et al. | 252/299.01 |
| 5,118,586 | 6/1992 | Hattori et al. | 430/20 |

OTHER PUBLICATIONS

Photo- and Thermo-Chromic Liquid Crystal Polymers with Spiropyran Groups, Cabresa et al., Mol. Cryst. Liq. Cryst., 155, 221-230 (1988).

*Primary Examiner*—Charles L. Bowers, Jr.
*Assistant Examiner*—John A. McPherson
*Attorney, Agent, or Firm*—Wolf, Greenfield & Sacks

[57] ABSTRACT

A photochromic material containing a copolymer of a spirobenzothiopyran derivative prepolymer and a liquid crystal prepolymer. In addition, a rewritable optical recording medium using the photochromic material. A rewritable optical recording medium obtained by coating a dispersed material, which is obtained by uniformly dispersing a spirobenzothiopyran derivative compound in a thermoplastic resin, on a substrate. A photochromic material capable of controlling a colored state and a decolorized state in a photon mode or a heat mode using an ultraviolet light source and a near-infrared light source. A rewritable optical recording medium capable of rewriting an information in a photon mode using a semiconductor laser.

11 Claims, 6 Drawing Sheets

ORDINATE: REFLECTANCE (10%/div)
ABSCISSA: (10μm/div)

(a): BEFORE ULTRAVIOLET IRRADIATION
(b): AFTER ULTRAVIOLET IRRADIATION

PHOTOCHROMIC MATERIAL AND REWRITABLE OPTICAL RECORDING MEDIUM

This application is a division of application Ser. No. 07/655,999 filed on Feb. 14, 1991 now U.S. Pat. No. 5,164,287.

BACKGROUND OF THE INVENTION

1. Field of the Invention

The present invention relates to a photochromic material used as various kinds of recording material, displaying material, photographic printing material, optical filter, photometer, masking material and the like. In addition, the present invention relates to an optical recording medium used in for example an optical disk recording and regenerating apparatus (hereinafter referred to singly as recording and regenerating apparatus), in particular to a rewritable optical recording medium capable of not only writing in and reading out informations by the use of laser beams but also rewriting informations.

2. Description of Related Art

An optical disk, which is a disk optical recording medium used in a recording and regenerating apparatus usually has recording function but an addition-type optical disk incapable of erasing recorded informations after recording them and a rewritable optical disk capable of erasing recorded informations after recording them to record other informations again have been known. The recording and regenerating apparatus using such the optical disks have been usually used as an outside memory of an electronic computer.

The addition-type optical disk comprises a substrate made of glass or plastic and a metallic vapor deposited layer, such as a tellurium (Te) vapor deposited layer, having a low melting point and formed on the substrate as a recording medium. In a recording and regenerating apparatus using this, the addition-type optical disk is rotated at a high speed to collect laser beams optically modulated depending upon informations to be written in onto the metallic vapor deposited layer as a light absorptive layer, whereby subjecting the metallic vapor deposited layer to a thermal processing, in short the metallic vapor deposited layer is punched to write in the informations. In the addition-type optical disk, the informations are written in the metallic vapor deposited layer by the thermal processing, as above described, so that it is impossible to erase the informations recorded once.

On the other hand, in the rewritable optical disk, a photomagnetic effect, for example Kerr effect, and a crystalline-amorphous phase transition have been utilized according to circumstances. For example, in a recording and regenerating apparatus using the rewritable optical disk utilizing the phase transition, the rewritable optical disk provided with a tellurium family amorphous metallic layer formed as the recording medium on the surface of the substrate is rotated at a high speed to collect laser beams optically modulated depending upon informations to be written in onto the amorphous metallic layer, whereby producing the phase transition in the amorphous metallic layer to write the informations in the amorphous metallic layer. And, in order to erase the recorded informations, the phase transition is produced again in the amorphous metallic layer by the utilization of a heat of laser beams to return the amorphous metallic layer to the original condition (Japanese Patent Application Laid-Open No. Sho 62-165749 and Japanese Patent Application Laid-Open No. Sho 62-165750). As above described, in case of the conventional rewritable optical disk, the writing in piles can be conducted by merely irradiating with lights and characteristics of a noncontact optical recording can be perfectly kept, which are preferable.

A photochromic material composing such the rewritable optical recording medium is a material, which is colored by irradiating ultraviolet rays and decolorized by an irradiation of visible rays and a heat, and is made by dispersing a photochromic compound in a solution or a high molecular medium or carrying the photochromic compound on the high molecular medium by a chemical bond. It has been known that in particular the material made by carrying the photochromic compound on the high molecular medium by a chemical bond can suppress an elusion of the photochromic compound from the medium and thus a heat stability of a colored body can be improved [refer to for example Kobunshi Ronbunshu., 33, 649 (1976)].

In addition, it has been disclosed in Mol. Cryst. Liq. Cryst., 1988, Vol. 155, pp 221-230 that a side chain-type high molecular liquid crystal photochromic material exhibits a photochromism and a thermophotochromism. On the other hand, sulfur-containing spiropyran has been proposed as a photochromic compound having a sensitivity to a near infrared range [refer to for example Journal of Physical Chemistry., Vol. 72, No. 3 (1968), pp. 997-1001]. This photochromic compound is reversibly colored and decolorized in a photon mode.

The photochromic material usable in the rewritable optical recording medium must be superior in repeated applicability of at least colorless→colored and colored→colorless and have an increased color-changing speed when irradiated with a light not less than a threshold value but not be discolored when irradiated with a light less than the threshold value and superior in preservative stability under the colorless condition and the colored condition, so that it is limited by a spirobenzothiopyran derivative compound. However, the spiropyran compound usually exhibits the following basic problems:

1. The sulfur-containing spiropyran is remarkably inferior in durability to the repeated application of coloring and decolorization and the colored body is unstable to heat. In addition, in the case where sulfur-containing spiropyran is used for the optical recording material, the recorded informations are broken by a reading-out light according to circumstances because of the photon-mode recording.

2. The spiropyran compound is crystalline under the monomeric condition and a coating is associated with it, so that a resolution power of the optical recording medium (as for the optical disk, a diameter of 1 bit is about 1 $\mu$m) can not be sufficiently enhanced.

3. The colored spiropyran compound is usually thermally unstable to be isomerized into a colorless body, so that it is insufficient in preservative stability.

SUMMARY OF THE INVENTION

The present inventors have found that it is advantageous to uniformly disperse the spiropyran compound in a high molecular matrix in order to solve the above-described problem 2 and it is advantageous for this object to uniformly disperse the sipropyran groups in the high molecular matrix, as disclosed in Japanese Patent Application Laid-Open No. Hei 1-294090. In addition, the present inventors have paid attention to that it is necessary to give a thermal stability to the compound itself in order to solve the above-described problem 3 and it had better introduce hydroxyl groups into the spiropyran compound to utilize hydrogen bounds for this object, as disclosed in Journal of the Chemical Society Chemical Communication., p. 437 (1986). The present invention has been achieved on the basis of such the circumstances in order to solve the above described problems.

It is one object of the present invention to provide a photochromic material improved in stability under the colored condition and remarkably easy to control the colored condition and decolorized condition thereof.

It is another object of the present invention to provide a photochromic material capable of controlling the colored condition and decolorized condition thereof in a photon mode and a heat mode by the use of a light source (for example a semiconductor laser) of ultraviolet range and near-infrared range.

It is a further object of the present invention to provide a photochromic material capable of realizing a thermal stability by the use of inexpensive organic materials.

It is a still further object of the present invention to provide a rewritable optical recording medium capable of rewriting informations in a photon mode by the use of a semiconductor laser utilizing photochromic characteristics.

It is still another object of the present invention to provide a rewritable optical recording medium capable of producing from inexpensive organic materials.

The photochromic material according to the present invention is characterized in containing a copolymer of a spirobenzothiopyran derivative prepolymer expressed by the following formula (I) and a liquid crystal prepolymer expressed by the following formula (II):

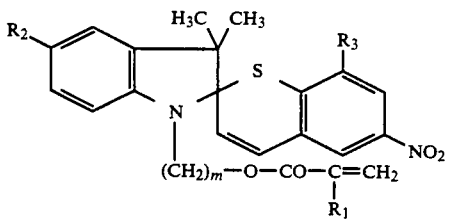

wherein $R_1$ is a hydrogen atom or a methyl group; $R_2$, $R_3$ are respectively hydrogen atom, a hydroxyl group, a halogen atom, an amino group, a lower alkoxy group or an aryl group, $R_2$ is same as or different from $R_3$; and m is an integer of 1 to 20.

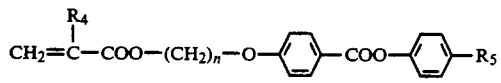 (II)

wherein $R_4$ is a hydrogen atom or a methyl group; $R_5$ is a nitryl group, a lower alkoxy group,

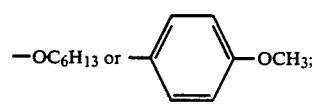

and n is an integer of 1 to 20.

In addition, the rewritable optical recording medium according to the present invention is characterized in using the above-described photochromic material having such the structure.

Further, another rewritable optical recording medium according to the present invention is characterized in producing by uniformly dispersing a spirobenzothiopyran derivative compound expressed by the following formula (III) in a thermoplastic resin and coating the resulting dispersed material on a substrate.

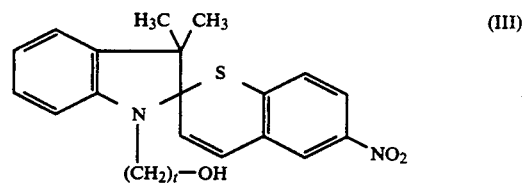

wherein t is an integer of 1 to 20.

The above and further objects and features of the invention will more fully be apparent from the following detailed description with accompanying drawings.

BRIEF DESCRIPTION OF THE DRAWINGS

FIG. 9 is a graph showing results of a reading conducted by the semiconductor laser beam for the rewritable optical recording medium according to the present invention which has been subjected to the writing-in.

DESCRIPTION OF THE PREFERRED EMBODIMENTS

Figure 1:
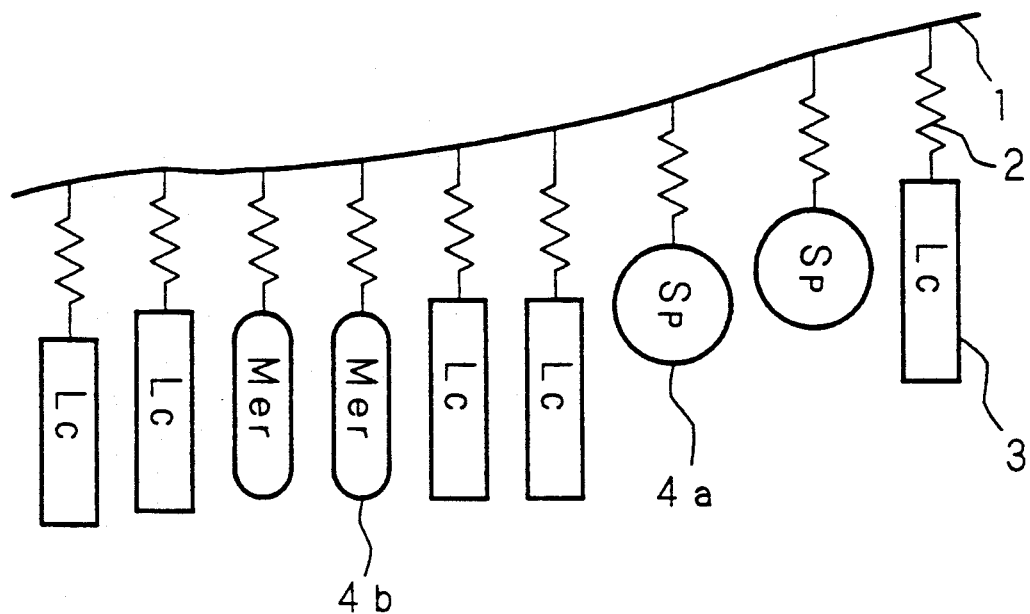
FIG. 1 is a schematic diagram showing a copolymer used in a photochromic material according to the present invention.

The photochromic material according to the present invention contains a copolymer of a spirobenzothiopyran derivative prepolymer expressed by the following formula (I) and a liquid crystal prepolymer expressed by the following formula (II):

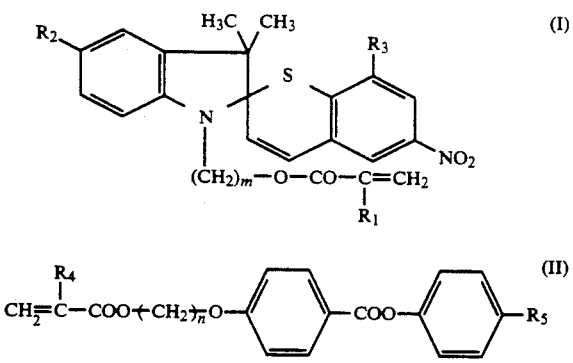

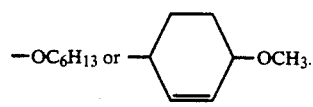

The spirobenzothiopyran derivative prepolymer [hereinafter referred to as prepolymer (A)] expressed by the general formula (I) is an ingredient for realizing the photochromism. In the general formula (I), $R_1$ is a hydrogen atom or a methyl group; $R_2$, $R_3$ are a hydrogen atom, a hydroxyl group, a halogen atom, an amino group, a lower alkoxy group or an aryl group, respectively, $R_2$ being same as or different from $R_3$. Concretely, the lower alkoxy group and aryl group include a methoxy group, an ethoxy group, a phenyl group, a tolyl group, a xylyl group, a naphthyl group and the like. In addition, m is an integer of 1 to 20, preferable 1 to 6. Because it is found from the experimental results that both a photoresponse speed and a thermoresponse speed are increased with an increase of m and if m is larger than 20, the photoresponse speed is increased but also a thermal reaction-inhibiting effect by a mesogen group is reduced, which is not becoming to the objects of the present invention.

Concrete examples of the prepolymer (A) include for example

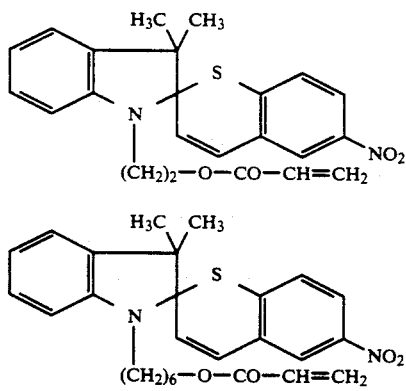

A synthetic method of the prepolymer (A) is not specially limited. It can be synthesized according to for example a method of S. Arakawa et al. [refer to Chem. Lett., 1905 (1985)] and a method of J. Vorborgt et al. [refer to J. Polym. Sci. Polym. Chem. Ed., 12, 2511 (1974)].

The liquid crystal prepolymer [hereinafter referred to as prepolymer (B)] expressed by the general formula (II) is an ingredient for increasing the thermal stability. In the general formula (II), $R_4$ is a hydrogen atom or a methyl group and $R_5$ is a nitryl group, a lower alkoxy group, Concrete examples of the lower alkoxy group include a methoxy group, an ethoxy group and the like. In addition, n is an integer of 1 to 20, preferably 1 to 6. If n is larger than 20, also the thermal reaction-inhibiting effect by the mesogen group for a photochromic group is reduced in the same manner as for m, which is not becoming to the objects of the present invention.

Concrete examples of the prepolymer (B) include

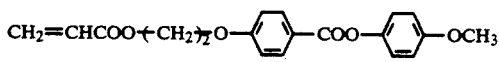

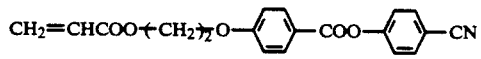

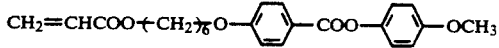

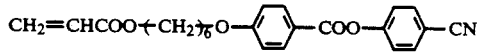

and the like.

A synthetic method of the prepolymer (B) is not specially limited. It can be synthesized according to for example a method of M. Portugall et al. [refer to Macromol. Chem., 183, 2311 (1982)].

It is sufficient that the copolymer contained in the photochromic material according to the present invention is obtained by copolymerizing the prepolymer (A) and the prepolymer (B) in a ratio so as to exhibit a smectic condition or a nematic condition. In view of this point, it is preferable that the copolymer is obtained by copolymerizing the prepolymer (A) and the prepolymer (B) in a ratio of 1 to 50, in particular 10 to 30,: 100 parts by weight.

Furthermore, a length of spacer m and n in the prepolymer (A) and the prepolymer (B) may be different to each other but it is preferable in view of a matter that the length capable of putting the photochromic group between groups (hereinafter referred to as Lc) introduced into the copolymer by the prepolymer (B) containing the mesogen group is preferable that m is same as n.

Also a polymerization degree of the copolymer is not limited but the polymerization degree gives an influence upon a temperature range exhibiting a liquid crystallinity, so that it is preferable that the polymerization degree becoming to an object of the material used is selected.

A method of producing the copolymer is not specially limited. It can be produced by the conventional polymerization methods.

The obtained copolymer is schematically shown in FIG. 1. Referring to FIG. 1, reference numeral 1 designates a main chain formed by copolymerizing the prepolymer (A) and the prepolymer (B). The main chain 1 comprises the mesogen group 3 introduced by the prepolymer (B), a photochromic group I 4a, which is a spiropyran group introduced by the prepolymer (A), and a photochromic group II 4b introduced from the photochromic group I 4a connected through spacers 2. In addition, Sp designates a ring-closure stable body, Mer designating a ring-opening stable body, and Mer being thermally stabilized by regularly orientating Lc.

The photochromic material containing a polymer according to the present invention is greatestly characterized in being capable of giving a threshold value to the photoisomerization reaction, suppressing the thermoisomerization reaction, and thus achieving the appointed objects. In short, as to the coloring and decolorization of the photochromic material according to the present invention, it goes without saying that the colored condition can be obtained by irradiating with ultraviolet rays and the decolorized condition can be obtained by irradiating with strong near-infrared rays and this transition can be repeated many times. The colored condition is difficulty returned to the decolorized condition by irradiating with relatively weak near-infrared rays and visible rays.

The preferred embodiments of the photochromic material according to the present invention will be below described.

The spirobenzothiopyran derivative prepolymer [prepolymer (A)] is synthesized in the following manner.

In short, 5-nitrothiosalicylaldehyde is synthesized in the following procedures according to the method of S. Arakawa et al.

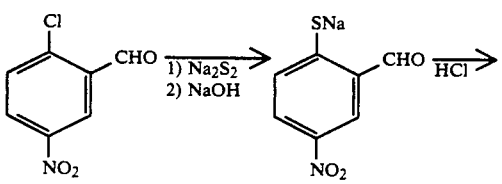

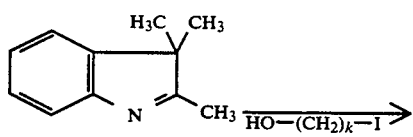

Then, spirobenzothiopyran derivative is synthesized in the following procedures according to the method of J. Vorborgt et al.

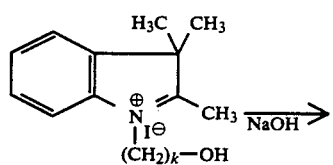

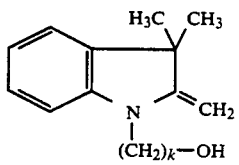

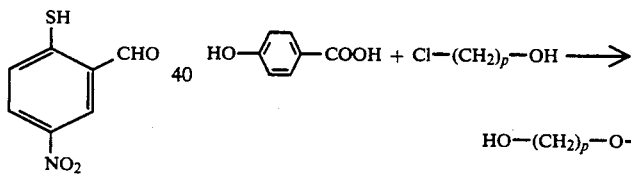

wherein k is 2, 3 or 6.

The liquid crystal prepolymer [prepolymer (B)] is synthesized in the following procedures according to the method of M. Portugall et al.

$$HO-\langle\rangle-COOH + Cl-(CH_2)_p-OH \longrightarrow$$

$$HO-(CH_2)_p-O-\langle\rangle-COOH$$

$$CH_2=CHCOOH + HO-(CH_2)_p-O-\langle\rangle-COOH \longrightarrow$$

$$CH_2=CHCOO-(CH_2)_p-O-\langle\rangle-COOH$$

$$CH_2=CHCOO-(CH_2)_p-O-\langle\rangle-COOH +$$

$$HO-\langle\rangle-R_6 \xrightarrow{SOCl_2}$$

$$CH_2=CHCOO-(CH_2)_p-O-\langle\rangle-COO-\langle\rangle-R_6$$

wherein p is 2, 3, 4 or 6; $R_6$ is CN or $OCH_3$.

One example of the identification results of the prepolymer (A) is shown in Table 1.

TABLE 1

| Compound | k | | Results of the elemental analysis (%) | | |
| --- | --- | --- | --- | --- | --- |
| | | | C | H | N |
| Prepolymer | 2 | calcd. | 65.39 | 5.25 | 6.63 |

TABLE 1-continued

| Compound | k | Results of the elemental analysis (%) | | |
|---|---|---|---|---|
| | | C | H | N |
| (A) | | found 66.25 | 5.09 | 6.46 |
| Prepolymer | 6 | calcd. 67.76 | 6.32 | 5.85 |
| (A) | | found 68.17 | 6.48 | 5.88 |

The prepolymer (A) of 0.2 mM and the prepolymer (B) of 2 mM, which have been obtained in this, are copolymerized in toluene of 10 ml with using AIBN of 2 mol % based on a total quantity of the prepolymer (A) and the prepolymer (B) as an initiator to obtain first to fifth copolymers shown in Table 2.

TABLE 2

| | k | p | $R_6$ | Polymerization degree |
|---|---|---|---|---|
| First copolymer | 2 | 2 | —OCH$_3$ | 20,000 |
| Second copolymer | 2 | 2 | —CN | 15,000 |
| Third copolymer | 3 | 3 | —CN | 20,000 |
| Fourth copolymer | 6 | 6 | —OCH$_3$ | 18,000 |
| Fifth copolymer | 6 | 6 | —CN | 20,000 |

The obtained respective copolymers (photochromic materials) of 3 mg are placed on a glass plate to be molten at 100° C. and then covered with a cover glass to be uniformly spread, whereby preparing test pieces of 10 μm thick.

The prepared 5 test pieces are irradiated with ultraviolet rays (obtained by passing a light from a xenon lamp of 500 W through an ultraviolet filter) for 1 minute and a change of each test piece in color is investigated immediately after the irradiation and after storing in a darkroom for 3 months. The test pieces are yellow before the irradiation. The test pieces are all colored in green immediately after the irradiation of ultraviolet rays. In addition, the test pieces all hardly exhibit a change of color before and after storing for 3 months in a darkroom.

Figure 2:
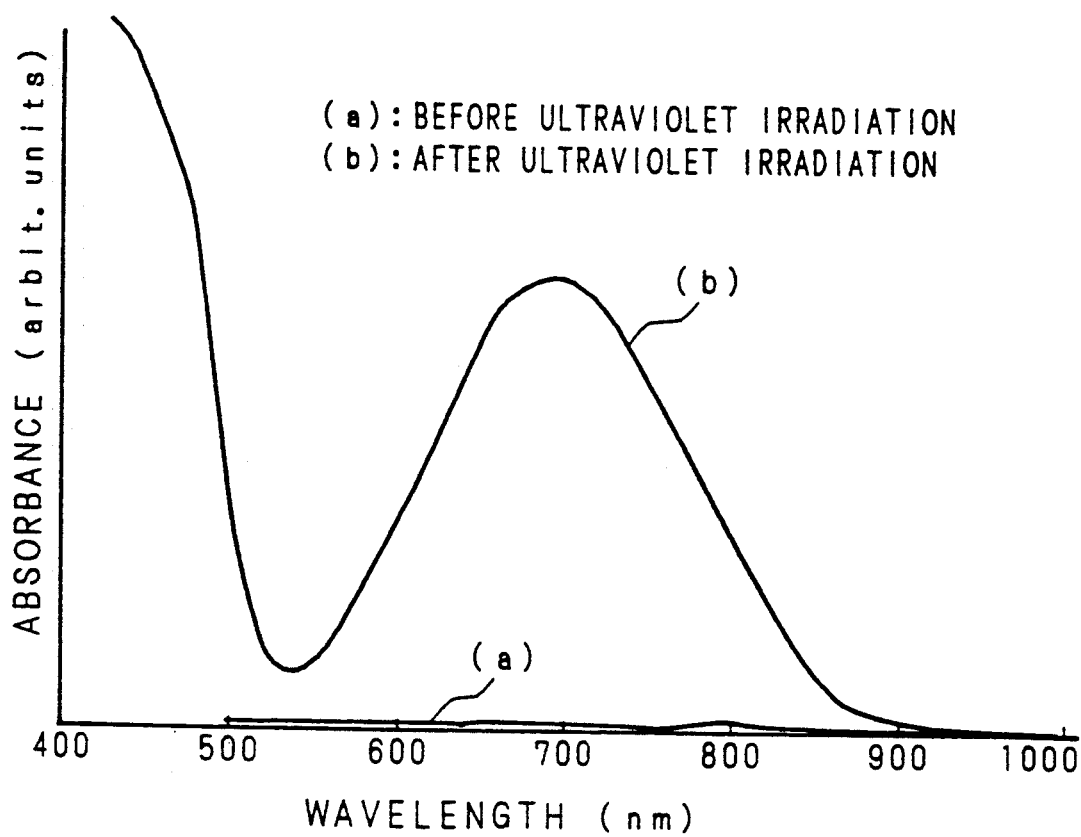
FIG. 2 is a graph showing a spectral change of the copolymer before and after irradiating with ultraviolet rays.

The test piece prepared from the first copolymer (first test piece) is investigated on an absorption spectrum at 25° C. before and after the irradiation of ultraviolet rays by using an absorption meter. The results are shown in FIG. 2. FIG. 2(a) shows an absorption spectrum of the test piece before the irradiation of ultraviolet rays. FIG. 2(b) shows an absorption spectrum of the test piece after the irradiation.

It is found from FIG. 2 that this material exhibits a photochromism and a colored body has an absorption peak at 705 nm and an absorption in a near-infrared range. In addition, the $\lambda_{MAX}$ of the spirobenzothiopyran derivative prepolymer is 680 nm. It is found that the absorption peak of the photochromic material according to the present invention is shifted to a long wavelength side by 25 nm.

In addition, upon irradiating the first test piece, which has been irradiated with ultraviolet rays, with visible rays, the absorption spectrum of the first test piece is returned to that before the irradiation of ultraviolet rays and this can be repeated many times.

Figure 3:
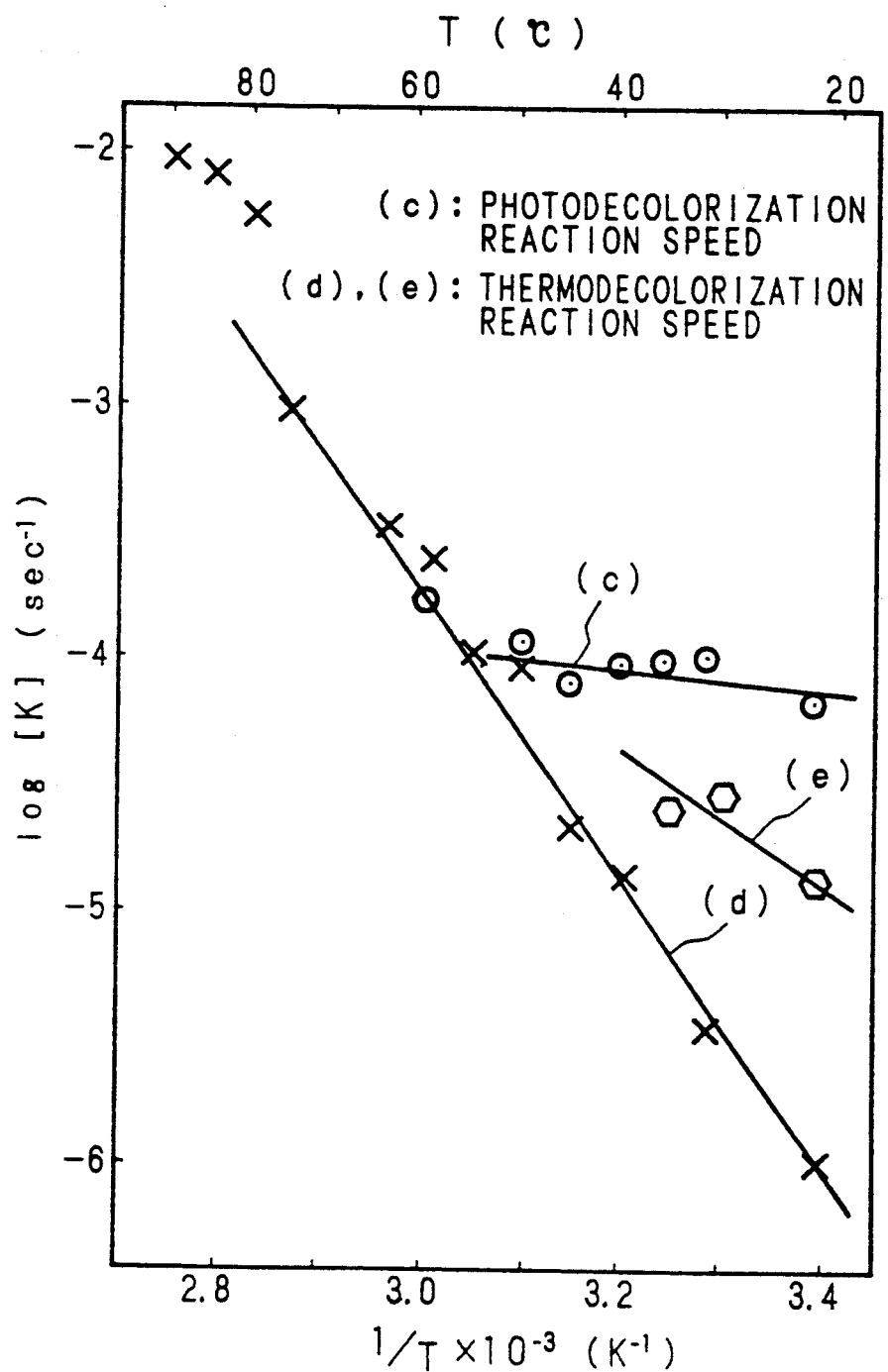
FIG. 3 is a graph plotted in accordance with the Arrhenius' equation of a reaction speed of a photo- and thermodecolorization of the copolymer.

A reaction speed [K] in the photodecolorization and the thermodecolorization of the first test piece is determined from a change of a light having a wavelength of 680 nm, which had passed through the colored body under the irradiation of visible rays, with a lapse of time. The Arrhenius' plot of the photodecolorization reaction process and the thermodecolorization reaction process is shown in FIG. 3. FIG. 3(c) shows the photodecolorization reaction process and FIGS. 3(d), (e) show the thermodecolorization reaction process.

It is found from FIG. 3 that the first copolymer is nematic at 80° C. or more and glassy nematic at temperatures lower than 80° C. and the thermodecolorization speed of the process (d) at a room temperature is remarkably reduced. It seems that the thermodecolorization process (e) includes a process which is not stabilized by Lc.

Figure 4:
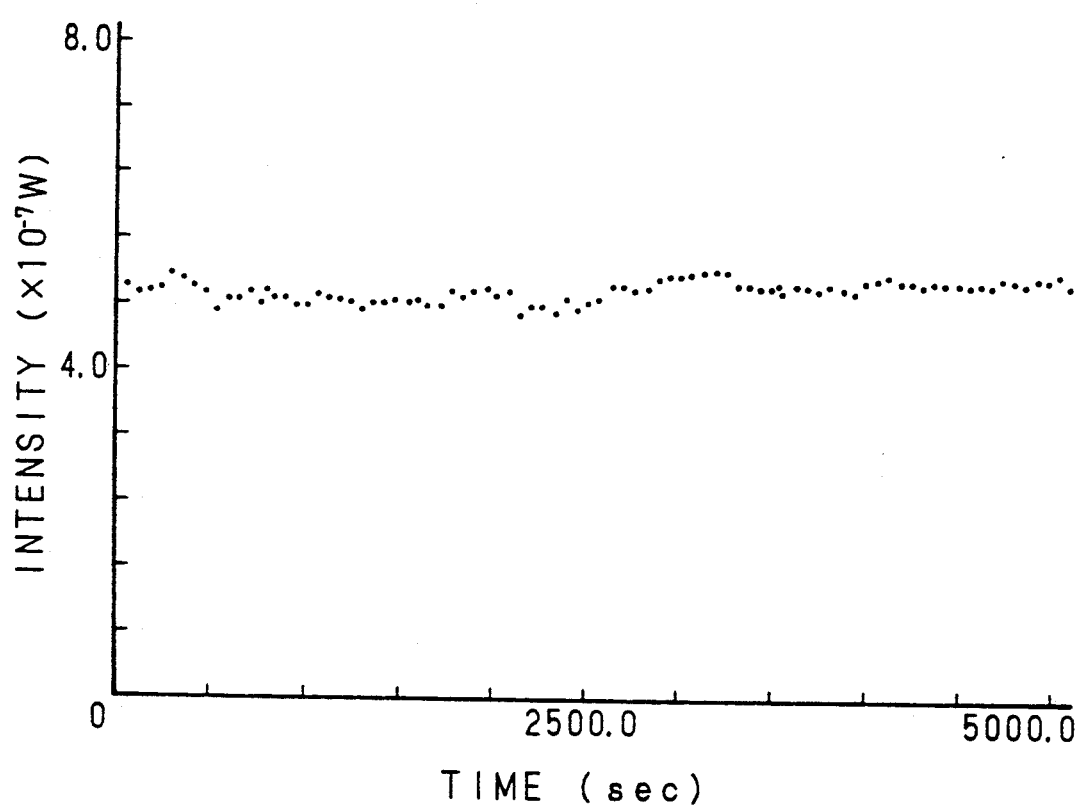
FIG. 4 is a graph showing a change of the copolymer in colored condition with the lapse of time at a reduced intensity of ultraviolet rays.

In addition, a change of an absorption of the light having a wavelength of 680 nm is measured when an intensity of ultraviolet rays is reduced to 5% of the above described one. The results are shown in FIG. 4. It is found from FIG. 4 that the colored body can not be obtained if ultraviolet rays are weak.

This is similar also to an intensity of visible rays in the obtainment of a colorless body.

It is found from the above-described results that the photochromic material according to the present invention exhibits a photochromism and the colored condition is thermally stable and additionally the colored condition and decolorized condition can be controlled by an intensity of light.

The first copolymer (200 mg) is dissolved in tetrahydrofuran (2 ml) to be applied to a non-grooved glass plate having a diameter of 130 mm by the spin coating method. A film-thickness is about 1 μm after drying. The resulting film is annealed for 10 minutes at 80° C. and then aluminum is vacuum vapor coated (about 550 Å) on the film as a reflecting film to obtain an optical recording medium.

As to a recording method, at first the optical recording medium is irradiated with ultraviolet rays using a black light to color all over the surface thereof and a signal is recorded (decolorized) on the optical recording medium by a semiconductor laser. The recording conditions are as follows: a wavelength: 780 nm; a power: 14 to 20 mW; a beam half band width: 1.3 μm; a linear velocity: 3.85 m/s; a frequency of carrier: 100 kHz to 1 MHz; a duty ratio: 50%; and a regenerating power: 1 mW.

Figure 5:
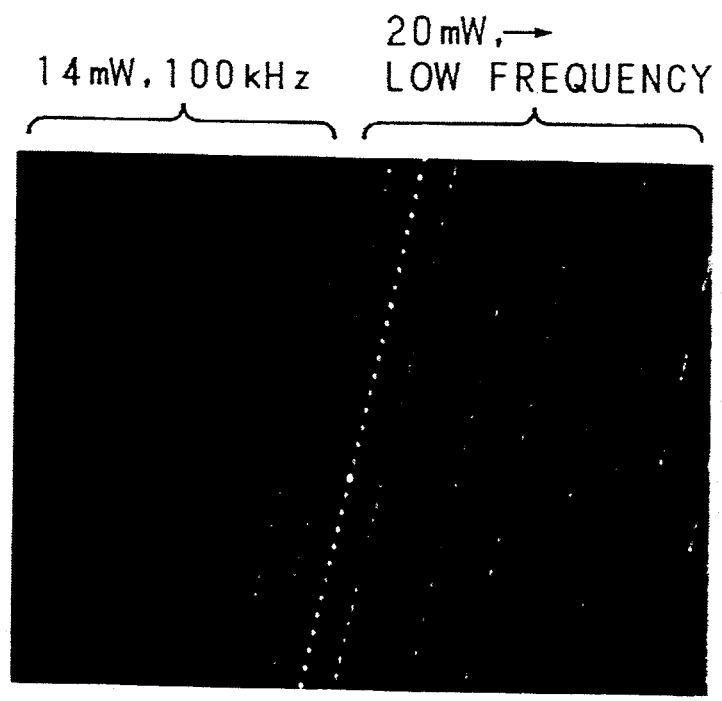
FIG. 5 is a microscopic photograph showing dots recorded on a rewritable optical recording medium according to the present invention.

FIG. 5 is a microscopic photograph showing a recorded dot recorded by a power of 14 to 20 mW and a sweeping signal of 100 kHz to 1 MHz. A width between recording lines is about 1 μm. A portion expressed by a light white line on a left side of the photograph is written-in at 14 mW and 100 kHz and a right portion is recorded at 20 mW. The record at 20 mW and 1 MHz exhibites a C/N ratio of 27 dB. In addition, it is found that the record could not be achieved under the above described conditions at a recording power of 14 mW or less and the recording power has a threshold value. That is to say, a recording sensitivity is 350 to 500 mJ/cm$^2$.

Figure 6:
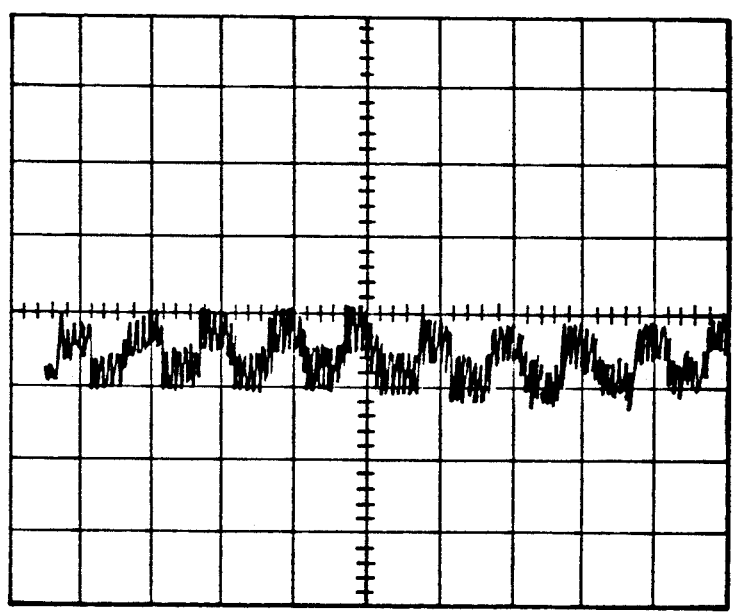
FIG. 6 is a photograph showing a signal regenerated from the rewritable optical recording medium according to the present invention.

Furthermore, as to the regeneration, it is found that the regeneration can be continuously repeated about 6,000 times at a regenerating power of 1 mW. FIG. 6 is a photograph showing a regenerated signal.

Besides, it is confirmed also that this record can be erased by irradiating with ultraviolet rays using the black light again and repeatedly recorded by means of the semiconductor laser. In addition, a stability in preservation of the record already clears 150 days at a room temperature.

It can be found from the above described results of recording test that the rewritable optical recording medium, to which the photochromism according to the preferred embodiments of the present invention is applied, is superior.

In addition, the regenerating stability can be still more increased under the thermally mild conditions. Furthermore, the substrate used here is provided with no groove and no high-refractive index layer but it is sure that if the substrate is provided with them, the C/N ratio and the recording sensitivity are still more improved.

As above described, since the photochromic material according to the present invention has a high stability of colored condition and gives a threshold value to the photoisomerization reaction, the colored condition and the decolorized condition can be very easily controlled. Accordingly, the optical recording medium using the photochromic material according to the present invention is superior. In addition, the photochromic material according to the present invention can be used as various kinds of recording memorizing material, the displaying material for the display and the like, the photographic printing material, the optical filter, the photometer, the masking material and the like.

Next, the rewritable optical recording medium according to another preferred embodiment of the present invention will be described.

In the rewritable optical recording medium according to this preferred embodiment, a spirobenzothiopyran derivative compound expressed by the following formula (III) is used as the photochromic material.

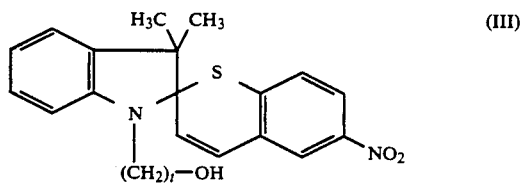 (III)

In the teneral formula (III), t is an integer of 1 to 20, preferably about 1 to 6. Because it is found from the experimental results that both a photoresponse speed and a thermoreactive speed are increased with an increase of t and if t is larger than 20, the photoresponse speed is increased but also a thermal reaction-inhibiting effect by a thermoplastic resin used together is reduced to make the achievement of the objects of the present invention difficult.

Of such the compound expressed by the general formula (III), those, in which t is 1, 2, 3, 4 or 6 are preferably used.

In addition, the compound expressed by the general formula (III) has been found as the optimum one of spiropyran compounds expressed by the following formula (IV) superior in stability of the record preservation and repeated use and showing a relatively high photoresponse speed in view of photorecording use.

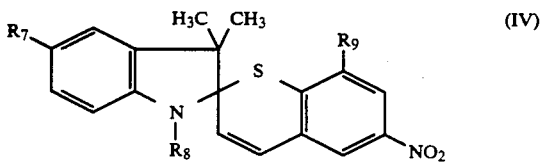 (IV)

wherein at least one of $R_7$, $R_8$ and $R_9$ has a hydroxyl group; others are any one of a hydrogen atom, a halogen group, a nitro group, an amino group, an alkyl group, an alkoxy group and an aryl group.

A synthetic method of the compound expressed by the general formula (III) is not specially limited. It can be synthesized according to for example a method of S. Arakawa et al. [refer to Chem. Lett., 1905 (1985)] and a method of J. Vorborgt et al. [refer to J. Polym. Sci. Polym. Chem. Ed., 12, 2511 (1974)].

The thermoplastic resin used in this preferred embodiment is an ingredient used as a matrix and its concrete examples include styrene resins, such as polystyrene, acrylic resins, such as polymethyl methacrylate, polyester resins, polyamide resins, polyethylene, polypropylene, polyvinylidene fluoride, polyvinylidene chloride, polyvinyl chloride, ethylene-vinyl acetate copolymers, vinyl chloride-vinyl acetate copolymer, styrene-acryl copolymers, styrene-butadiene copolymers, styrene-vinylidene chloride copolymers, styrene-vinyl chloride copolymers, epoxy resins, polycarbonate resins, mixtures thereof and the like but it is not limited by them.

It is preferable that a glass transition temperature (Tg) of the thermoplastic resin is 50° C. or more. Because it is necessary that the Tg is at least a temperature of natural environment and the thermoplastic resin is used under a glassy state of high molecule without fail, that is a segmental movement is inhibited, and, if the segmental movement is released, the thermoisomerization reaction of the compound expressed by the general formula (III) [hereinafter referred to as compound (III)] is promoted to make the achievement of the desired ends impossible.

The rewritable optical recording medium according to this preferred embodiment has a construction that a dispersed material with the compound (III) uniformly dispersed in the thermoplastic resin [hereinafter referred to as dispersed material (III)] is coated on a substrate.

It is preferable that the compound (III) is used in a quantity of 10 to 200 parts in usual, in particular 10 to 50 parts, based on 100 parts of the thermoplastic resin.

A method of uniformly dispersing is not specially limited. It is sufficient that for example the thermoplastic resin and the compound (III) are dissolved in solvents such as toluene, xylene and tetrahydrofuran.

Every light-transmissive or light-reflecting substrate, which has been generally used for the rewritable optical recording medium, made of for example glass, ceramics, metals, plastics and the like can be used as the substrate.

Also a method of coating the dispersed material (III) on the substrate is not specially limited. For example, a method, in which the thermoplastic resin and the compound (III) are dissolved in the solvents and the resulting solution is coated on the substrate by the spraying method and the like followed by drying, can be used.

It is preferable in view of using the recording and regenerating method by a laser beam that a film-thickness of a coating formed in such the manner is 0.3 to 3.0 μm as usual.

In the rewritable optical recording medium according to this preferred embodiment, for example an aluminum film of about 0.2 to 1 μm thick may be formed on the coating by the usual methods such as vacuum vapor coating method.

The record of informations into the rewritable optical recording medium according to such the preferred embodiment can be achieved by at first initializing the medium by means of ultraviolet rays having a wavelength of 380 nm at a recording sensitivity of about 1 J/cm² and then irradiating the recorded portion with a collected strong visible ray having a power of about 3 to 20 mW to make the recorded portion colorless.

And, the recorded informations can be regenerated by discriminating an existence of coloring in each bit by a relatively weak light having a wavelength of about 600 to 800 nm and a power of about 0.2 to 0.8 mW. The discrimination of an existence of coloring may be conducted by any one of a transmitted light and a reflected light.

In addition, a light source for recording, regenerating or erasing the informations includes a laser, a mercury lamp, a xenon lamp, a metal halide lamp, a halogen lamp, a tungsten lamp and the like. An optical filter may be used together.

The concrete production of the rewritable optical recording medium according to this preferred embodiment will be below described.

5-nitrothiosalicylaldehyde is synthesized in the following procedures according to the method of S. Arakawa et al.

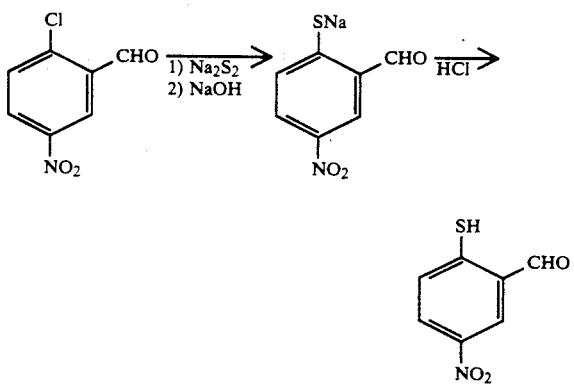

Then, the spirobenzothiopyran derivative compound is synthesized in the following procedures according to the method of J. Vorbogt et al.

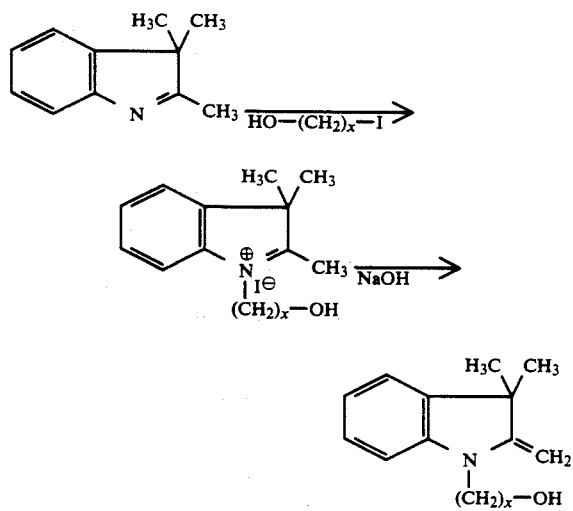

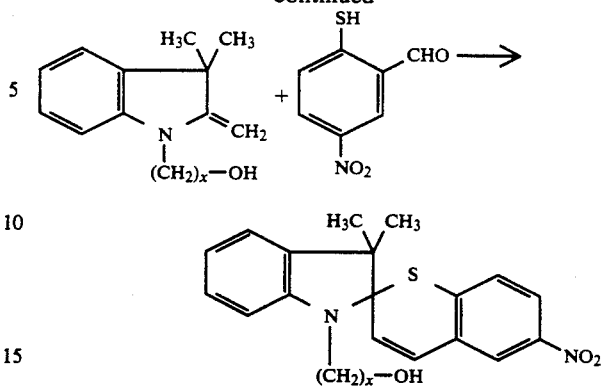

wherein x is 2 or 6.

The identification data (results of the elemental analysis) of the obtained spirobenzothiopyran derivative compound having x of 2 (hereinafter referred to as BTP-2) and the obtained spirobenzothiopyran derivative compound having x of 6 (hereinafter referred to as BTP-6) are shown in Table 3.

TABLE 3

| Compound | | Results of the elemental analysis (%) | | |
|---|---|---|---|---|
| | | C | H | N |
| BTP-2 | calcd. | 65.20 | 5.47 | 7.60 |
| | found | 61.69 | 4.59 | 5.06 |
| BTP-6 | calcd. | 67.90 | 6.65 | 6.60 |
| | found | 66.14 | 6.06 | 6.37 |

Polymethyl methacrylate (hereinafter referred to as PMMA) as the thermoplastic resin of 1 g or polystyrene as the thermoplastic resin of 1 g and BTP-2 of 285 mg or BTP-6 of 570 mg are dissolved in xylene of 8 g to prepare 4 kinds of composition. In addition, a composition composed of PMMA of 1 g, BTP-2 of 285 mg and xylene of 8 g is hereinafter referred to as BTP-2/PMMA.

The obtained compositions are coated on a glass substrate by the spray coating so that the film-thickness may be 1.0 μm after drying and then an aluminum layer of 0.5 μm thick is formed on the film by the vacuum vapor coating method to obtain rewritable optical recording mediums.

For the obtained rewritable optical recording mediums the measurement of a visible absorption spectrum, the microscopic observation and the reading and the reading test are conducted. The results are shown in FIGS. 7 to 9.

Figure 7:
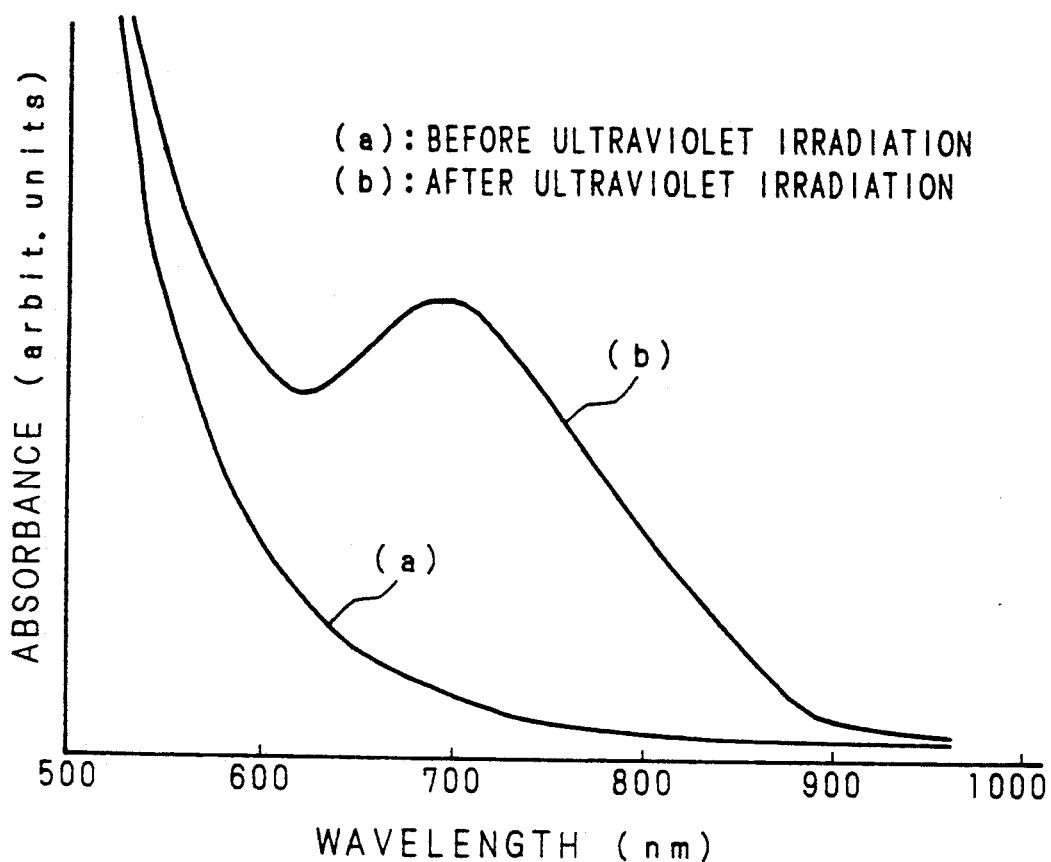
FIG. 7 is a graph showing a spectral change of the rewritable optical recording medium according to the present invention before and after irradiating with ultraviolet rays.

FIG. 7 is a graph showing a change of the rewritable optical recording medium using BTP-2/PMMA in visible absorption spectrum before and after irradiating with ultraviolet rays. The visible absorption spectrum is measured before [(a) in FIG. 7] and after [(b) in FIG. 7] irradiating the rewritable optical recording medium using BTP-2/PMMA with ultraviolet rays having a wavelength of 380 nm. It is found from FIG. 7 that this optical recording medium exhibits the photochromism and the colored body has the absorption peak in the vicinity of 690 nm and absorbs also a semiconductor laser beam having a wavelength of 780 nm.

Figure 8:
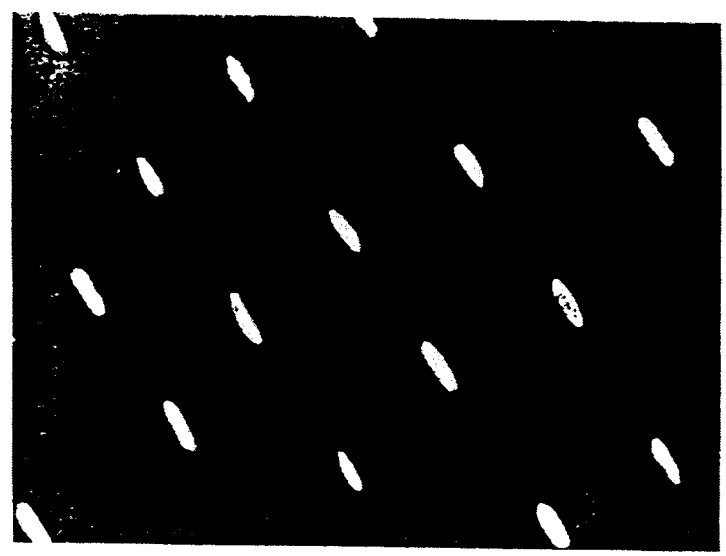
FIG. 8 is a microscopic photograph showing the rewritable optical recording medium according to the present invention after subjecting to a writing-in by a semiconductor laser beam.

FIG. 8 is a microscopic photograph of the rewritable optical recording medium using BTP-2/PMMA when written-in by a semiconductor laser beam. This rewritable optical recording medium is irradiated with ultraviolet rays having a wavelength of 380 nm and a power of 100 μW/cm² for 20 seconds to be initialized and then the writing-in is conducted by a semiconductor laser beam (780 nm) under the conditions that a power is 20 mW, a frequency being 100 kHz, and a rotational frequency being 600 r.p.m. followed by the microscopic observation. It is found from FIG. 8 that the colored body is black and the portions, which have been turned into colorless bodies by the irradiation of light, are white, which shows the achievement of the writing-in.

Figure 9:
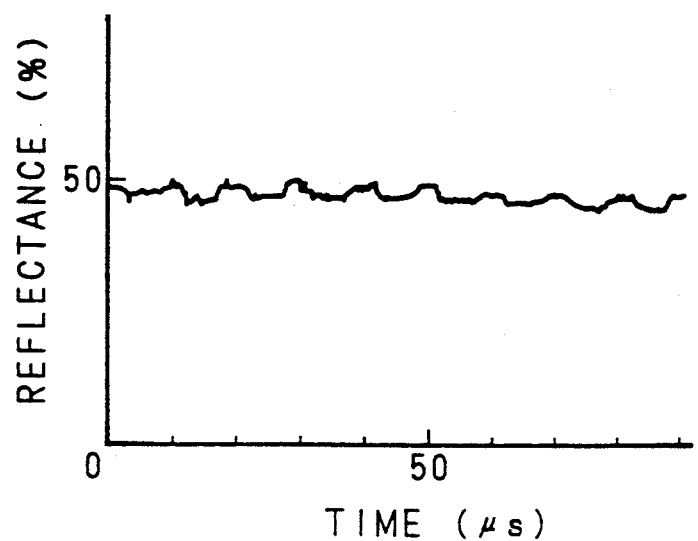

FIG. 9 is a graph showing results of the reading by a semiconductor laser beam after the writing-in for the rewritable optical recording medium using BTP-2/PMMA. In FIG. 9, an axis of ordinate shows a reflectance (%) and an axis of abscissa shows a time (μs). For this rewritable optical recording medium the writing-in is conducted under the same conditions as in the above-described microscopic observation and then irradiated with a semiconductor laser beam having a power of 0.8 mW and a wavelength of 780 nm at a rotational frequency of 600 r.p.m. to measure a reflectance of the semiconductor laser beam, whereby conducting the reading. It is found from FIG. 9 that the reflectance in the written-in portions is increased even after the reading 100 times, which shows the stabilized reading.

It is found from the above-described results that also the rewritable optical recording medium according to this preferred embodiment has superior characteristics.

As this invention may be embodied in several forms without departing from the spirit of essential characteristics thereof, the present embodiment is therefore illustrative and not restrictive, since the scope of the invention is defined by the appended claims rather than by the description preceding them, and all changes that fall within the metes and bounds of the claims, or equivalence of such metes and bounds thereof are therefore intended to be embraced by the claims.

What is claimed is:

1. A rewritable optical recording medium comprising a photochromic material containing a copolymer of a spirobenzothiopyran derivative prepolymer expressed by the following formula (I) and a liquid crystal prepolymer expressed by the following formula (II):

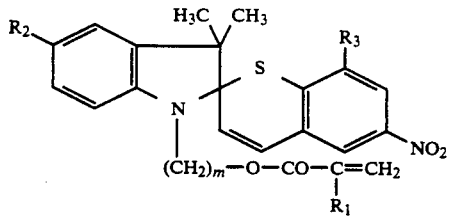

wherein $R_1$ is selected from the group consisting of a hydrogen atom and a methyl group;

$R_2$ is selected from the group consisting of a hydrogen atom, a hydroxyl group, a halogen atom, an amino group, a lower alkoxy group and an aryl group;

$R_3$ is selected from the group consisting of a hydrogen atom, a hydroxyl group, a halogen atom, an amino group, a lower alkoxy group and an aryl group; and m is an integer of 1 to 20;

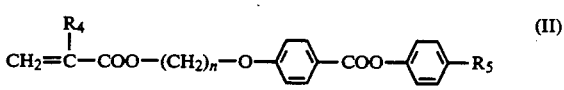

wherein $R_4$ is selected from the group consisting of a hydrogen atom and a methyl group;

$R_5$ is selected from the group consisting of a nitryl group, a lower alkoxy group,

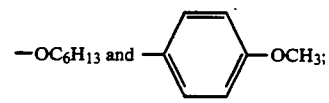

and n is an integer of 1 to 20.

2. A rewritable optical recording medium as set forth in claim 1 wherein m is an integer of 1 to 6.

3. A rewritable optical recording medium as set forth in claim 1 wherein m is 2 and $R_1$, $R_2$ and $R_3$ are all a hydrogen atom.

4. A rewritable optical recording medium as set forth in claim 1 wherein m is 6 and $R_1$, $R_2$ and $R_3$ are all a hydrogen atom.

5. A rewritable optical recording medium as set forth in claim 1 wherein n is an integer of 1 to 6.

6. A rewritable optical recording medium as set forth in claim 1 wherein n is 2, $R_4$ is a hydrogen atom and $R_5$ is —$OCH_3$.

7. A rewritable optical recording medium as set forth in claim 1 wherein n is 2, $R_4$ is a hydrogen atom and $R_5$ is —CN.

8. A rewritable optical recording medium as set forth in claim 1 wherein n is 6, $R_4$ is a hydrogen atom and $R_5$ is —$OCH_3$.

9. A rewritable optical recording medium as set forth in claim 1 wherein n is 6, $R_4$ is a hydrogen atom and $R_5$ is —CN.

10. A rewritable optical recording medium as set forth in claim 1 wherein m and n have the same value.

11. A rewritable optical recording medium as set forth in claim 1 wherein said spirobenzothiopyran derivative prepolymer is used in a quantity of 1 to 50 parts by weight based on 100 parts by weight of said liquid crystal prepolymer.

* * * * *

UNITED STATES PATENT AND TRADEMARK OFFICE
CERTIFICATE OF CORRECTION

PATENT NO. : 5,234,799

DATED : August 10, 1993

INVENTOR(S) : Suguru Nagae, Sei Tsunoda, Kenji Nomura, Kazuhiko Tsutsumi & Yoshiyuki Nakaki It is certified that error appears in the above-identified patent and that said Letters Patent is hereby corrected as shown below:

Title page Item [75] inventors, please change "Sei Tsuroda" to -- Sei Tsunoda --.

Signed and Sealed this

Third Day of May, 1994

Attest:

BRUCE LEHMAN

Attesting Officer

Commissioner of Patents and Trademarks